(12) United States Patent
Kelleher et al.

(10) Patent No.: US 7,493,803 B2
(45) Date of Patent: Feb. 24, 2009

(54) BALL PENETROMETER FOR SOFT SOILS TESTING

(75) Inventors: Patrick J. Kelleher, Coolac (AU); Stephen David Payor, Yagoona (AU); James Austin Shiels, Leonay (AU)

(73) Assignee: Benthic Geotech Pty Ltd., New South Wales (AU)

( * ) Notice: Subject to any disclaimer, the term of this patent is extended or adjusted under 35 U.S.C. 154(b) by 156 days.

(21) Appl. No.: 10/593,546

(22) PCT Filed: Feb. 25, 2005

(86) PCT No.: PCT/AU2005/000249

§ 371 (c)(1),
(2), (4) Date: Sep. 19, 2006

(87) PCT Pub. No.: WO2005/090942

PCT Pub. Date: Sep. 29, 2005

(65) Prior Publication Data

US 2007/0125158 A1    Jun. 7, 2007

(30) Foreign Application Priority Data

Mar. 23, 2004   (AU) .............................. 2004901537

(51) Int. Cl.
*G01N 3/00* (2006.01)
(52) U.S. Cl. .......................................................... 73/84
(58) Field of Classification Search ...................... 73/84, 73/85

See application file for complete search history.

(56) References Cited

U.S. PATENT DOCUMENTS

| | | | | |
|---|---|---|---|---|
| 2,860,515 A * | 11/1958 | Brown | ........................ | 175/394 |
| 3,722,604 A * | 3/1973 | Lesher | ........................ | 175/19 |
| 4,382,384 A | 5/1983 | Mitchel et al. | ................ | 73/594 |
| 6,062,090 A | 5/2000 | Bachhuber et al. | ............ | 73/784 |
| 6,116,353 A | 9/2000 | Leavell et al. | ................. | 175/22 |
| 6,644,423 B2 * | 11/2003 | Bratton et al. | ................ | 175/58 |
| 7,040,146 B2 * | 5/2006 | Mackenzie et al. | ............. | 73/81 |
| 2005/0076709 A1 * | 4/2005 | Mackenzie et al. | ............. | 73/81 |

FOREIGN PATENT DOCUMENTS

WO    WO 9403682 A1 *    2/1994

\* cited by examiner

*Primary Examiner*—Hezron Williams
*Assistant Examiner*—Tamiko D Bellamy
(74) *Attorney, Agent, or Firm*—King & Schickli, PLLC

(57) ABSTRACT

A ball penetrometer probe for in situ measurement of soft soil properties, particularly in the seabed, comprises a spherical body and slender shaft assembly, and either individually or in combination, an anti-friction sleeve enclosing the shaft and/or a peripheral porous ring on the spherical body with connecting internal passages through the shaft assembly, the shaft being adapted to attach to an electronic transducer module. The ball penetrometer is deployed to penetrate the soil bed, to continuously measure the soil bearing forces resisting penetration and withdrawal of the ball, to optionally measure the pore water pressure of the soil in contact with the ball and to transmit the measurement data from the probe to a remote operating station, either by wireless means such as an acoustic transducer or via a wired electrical connection.

38 Claims, 1 Drawing Sheet

BALL PENETROMETER FOR SOFT SOILS TESTING

TECHNICAL FIELD

The present invention relates to a method and apparatus for investigating soil properties of soft soils, for example seabeds or other submerged beds such as lakebeds, etc., and in particular, to an improved ball-type penetrometer and associated method of use thereof.

BACKGROUND ART

Determining the soil characteristics of the seabed is an essential part of the geotechnical design of offshore installations, which can include structures for oil and gas developments, seabed anchorages, submarine pipelines and cables, and wind energy developments. The in situ properties of seabed soils profoundly influence the design and performance of structures that interact with the seabed. The trend in the offshore energy industry towards working in deep and ultra-deep water, where soft sediments predominate, places increasing importance on the ability to accurately measure soft soil strength and deformation parameters. Examples of prior art documents describing known techniques for seabed analysis include U.S. Pat. Nos. 5,127,261; 6,463,801 and 6,526,818.

Sediment strength profiles are commonly measured in situ using a variety of tools, deployed by various means including 'wireline' drillstring, coiled 'wheel-drive' tubes, seabed push frames and more recently by remotely operated seabed platforms. Tools commonly used to profile the shear strength of soft cohesive sediments include the cone penetrometer test (CPT) and vane shear test (VST). A relatively recent penetrometer device, known as the 'T-Bar', has also been deployed in the field. The T-Bar device has advantages over the conventional CPT and VST tools, in particular a closed form solution exists for undrained shear strength as a function of bar penetration resistance, and the geometry of the device also negates the need to correct for water pressure effects. In soft soils, these factors combine to reduce uncertainty in design and significantly enhance the resolution of the measured soil strength profile. However, all of the above tools have limitations.

Key disadvantages with the use of CPT devices in soft soils include:
a) cone correction factors, which are used to convert CPT tip resistance to soil shear strength, are empirically based and vary widely, depending on the type and state of the soil undergoing test. Uncertainties associated with the application of cone factors typically leads to a high degree of conservatism in design;
b) CPT devices (particularly when subjected to high ambient water pressures), require a correction for the effects of water pressure acting on the unequal areas of the cone tip. This correction is typically very significant in soft sediments, which mobilise relatively low cone tip pressures and high excess pore water pressures;
c) cone penetrometers have a relatively poor capacity to accurately profile soft sediments. They have relatively small tip areas (reducing the load mobilised on the cone tip load cell to typically less than a few MPa), and relatively high capacity load cells (sediments that mobilise tip pressures of 50 MPa or greater can usually be probed). These factors combine to reduce the available resolution of the device.

Disadvantages of the VST include:
a) the VST cannot provide a continuous measurement of the shear strength profile with depth;
b) the VST is not suitable for measuring the shear strength of dilatant, coarse grained soils;
c) knowledge of the soil type is required for correct interpretation of VST results.

A key disadvantage of the T-Bar penetrometer for deployment via a drillstring of relatively small diameter, lies with the required geometry of the horizontal bar. Research to date indicates that an aspect ratio (length/diameter) of typically 4 to 8 is required for accurate in situ measurement of soil strength. To provide sufficient bearing area of the bar, this means that bar lengths of more than 150 mm are usually required. This presents problems for many offshore drilling units, particularly remotely operated seabed drilling units, which currently are incapable of handling these large dimension tools.

The spherical ball penetrometer (SBP) is a known alternative device that offers the same fundamental benefits of the T-Bar, but without the associated problems of geometry as described above. The SBP offers a number of distinct advantages over conventional in situ test methods, which include the following:
a) there exists an exact solution for shear strength as a function of ball bearing resistance;
b) the ball bearing area is significantly greater than for a standard CPT tool—this means that much higher bearing forces are mobilised in soft sediment profiles, greatly enhancing the resolution of the measured shear strength profile;
c) there are no significant water pressure corrections required, simplifying data processing and reducing uncertainty of the measurements;
d) a measure of remoulded and cyclic shear strength degradation is also possible via static withdrawal and or cyclic loading of the tool following penetration into the soil.

Despite these advantages the SBP test has not been adopted for general field use and the present applicant is not aware of any published reports of its deployment in an offshore environment. SBP probes disclosed in the literature are individual dedicated instruments with simple built-in load cells close to the ball, with no capability for optional measurement of pore water pressure. Furthermore, presently known SBPs rely on wired electrical connections between the downhole probe and the surface equipment for power supply and data telemetry.

It would be advantageous to provide an improved ball penetrometer probe that is interchangeable with conventional CPT probes or the like, and has a reasonable cross sectional geometry suitable for both wireline deployment and for deployment using remotely operated seabed systems. In the latter case, such a tool can exploit the use of wireless data transmission, such as known acoustic methods, to transmit measurement data from the downhole probe to operators for real-time analysis and display. It is preferable to provide wireless data transmission so that the probe can be usefully employed on a seabed system that relies on remotely joining discrete lengths of drill pipe to advance the probe into the seabed soil formation.

As used herein, the phrase "remote operating station" generally refers to a surface vessel or platform, where the downhole data is ultimately received by a computer interface and human operator. In the case of a wireline system the remote operating station is connected directly to the downhole probe by wire(s) and/or cable(s) through the water column and the borehole. Another alternative for so-called "measurement while drilling" uses a "mud pulse" system that transmits data via pressure pulses in the drilling fluid up the drill string, however this is impractical for small diameter tools.

Also as used herein, the phrase "remotely operated seabed system" generally refers to the situation where the probe is deployed robotically or otherwise down the borehole from a seabed platform or other type of vehicle rather than manually from a surface platform. Communication from the probe to the seabed platform/system may be by wire(s), cable(s) and/or by wireless means. Communication between the seabed system and the surface vessel (i.e. the "remote operating station") is typically via wire and/or cable (eg. electrical or optical fibre telemetry).

Unlike standard CPT test data, SBP test data does not require a correction for pore water pressure. Nevertheless, it would be advantageous for a ball penetrometer to provide a capability to measure this parameter, as this enables dissipation testing to be undertaken at the discretion of the operator, negating the need to complete a second borehole using conventional CPT equipment. Dissipation testing is a standard means of measuring time-dependent soil drainage characteristics. The capability to measure dynamic pore pressure may also be employed to estimate the cyclic performance of soft soils subjected to cyclic loading. Additionally, or alternatively, it would also be advantageous for a ball penetrometer to avoid complications due to relative movement of the soil in contact with the shaft, which normally gives rise to friction forces additional to the bearing forces acting on the ball.

This identifies a need for an improved ball-type penetrometer and method of use thereof which overcomes or at least ameliorates problems inherent in the prior art.

The reference to any prior art in this specification is not, and should not be taken as, an acknowledgment or any form of suggestion that such prior art forms part of the common general knowledge.

DISCLOSURE OF INVENTION

The present invention aims to provide an improved ball penetrometer for use in measuring the in situ undrained strength of soft soils. A further aim of the invention is to provide a ball penetrometer probe that is interchangeable with a standard type of cone penetrometer probe or the like, suitable for use with surface deployed wireline equipment or with wireless equipment deployed by remotely operated seabed systems. In a further preferred, but non-essential form, the invention can provide a ball penetrometer probe with a pore water pressure measurement capability.

According to a particular embodiment of the present invention, the ball penetrometer includes a hardened, roughened spherical assembly rigidly attached on its axis of symmetry to the lower end of a cylindrical shaft, the shaft diameter being substantially smaller than the ball diameter and the shaft length being substantially greater than the ball diameter. The shaft is adapted at its upper end to attach to a module, for example a conventional type of electronic transducer module employed with standard cone penetrometers, for example as manufactured by Geotech AB and A.P. van den Berg BV. When the probe assembly is thrust into the soil bed, the reaction force acting on the ball is transmitted via the shaft to a load cell in the transducer module. The transducer output signals are transmitted to a remote operating station for display and analysis in real-time. This transmission may be accomplished by wireline methods, by wireless acoustic means, by electrical or electro-optical cable or by a combination of such methods.

Relative movement of the soil in contact with the shaft will normally give rise to friction forces additional to the bearing forces acting on the ball. For accurate interpretation of measurement data attributable to the spherical geometry alone, the shaft friction should preferably be eliminated. In a further preferred, but non-essential form, the invention provides that the shaft is enclosed by an antifriction sleeve.

Hence, according to different embodiments of the present invention, the penetrometer can provide, either individually or in combination, an anti-friction sleeve enclosing the shaft and/or a porous material provided with or as part of the spherical body with at least one connecting internal fluid passage through the spherical body and shaft assembly In one particular embodiment, the shaft is loosely enclosed by a tubular antifriction sleeve which is recessed at its lower end into the top of the ball and at its upper end into the outer sleeve of the transducer module. According to further aspects of a particular embodiment of the invention, the antifriction sleeve is peripherally sealed by flexible sealing members, for example o-rings, at each end. These o-ring seals accommodate minute axial displacement of the ball and shaft assembly arising from reaction forces on the ball during soil penetration and withdrawal. The ball and shaft assembly can thus freely sense the true axial load acting on the ball, in isolation from soil friction on the shaft. Load sensing is bi-directional, that is, measuring both downwards penetration into undisturbed soil and upwards thrust as a measure of remoulded shear strength.

According to the present invention, measurement of soil shear strength may be accompanied by measurement of pore water pressure, or vice versa. Known ball penetrometer probes do not provide this capability. According to a further particular embodiment of the present invention, there can be provided a peripheral ring of porous material around the ball. The porous ring connects via internal fluid-filled galleries in the ball and shaft to a pressure transducer in the attached electronics module. The porous ring allows the internal fluid pressure to equilibrate with the external fluid pressure surrounding the ball to provide measurement of dynamic pore water pressure. Preferably, the porous ring is optimally positioned at the mid-point of the ball where it is least affected by creep strain of soil during the course of dissipation testing.

Deployment of the ball penetrometer into a seabed, or the like, can be achieved by various means including 'wireline' drill string, coiled tubes, straight rods, anchored seabed frames and remotely operated vehicles or seabed platforms. According to a particular aspect of the present invention, the method of conducting a ball penetrometer test generally involves at least some of the steps of:

a) thrusting the ball penetrometer probe into the soft soil bed at a known rate, either commencing at mudline, or at some depth below mudline through drillstring or casing;
b) measuring bearing resistance of the soil on the ball versus penetration depth;
c) measuring the dynamic pore water pressure at the mid-point of the ball as the ball penetrates the soil;
d) withdrawing the ball penetrometer probe from the soil bed at discrete depth intervals and at a known rate;
e) measuring the bearing force resisting withdrawal of the ball from the soil bed as a function of depth;
f) where required, performing multiple compression and tension loading cycles to obtain a measure of the degradation characteristics of the soil;
g) concurrently recording measurement data from the probe and transmitting the same measurement data to a remote operating station;
h) recovering the ball penetrometer probe.

When deployed from a remotely operated seabed platform, the penetration depth of the ball penetrometer into the seabed may be progressively extended during a test by joining of a series of connector rods or drill pipes.

BRIEF DESCRIPTION OF FIGURES

The present invention should become apparent from the following description, which is given by way of example only, of a preferred but non-limiting embodiment thereof, described in connection with the accompanying figure.

MODES FOR CARRYING OUT THE INVENTION

Figure 1:
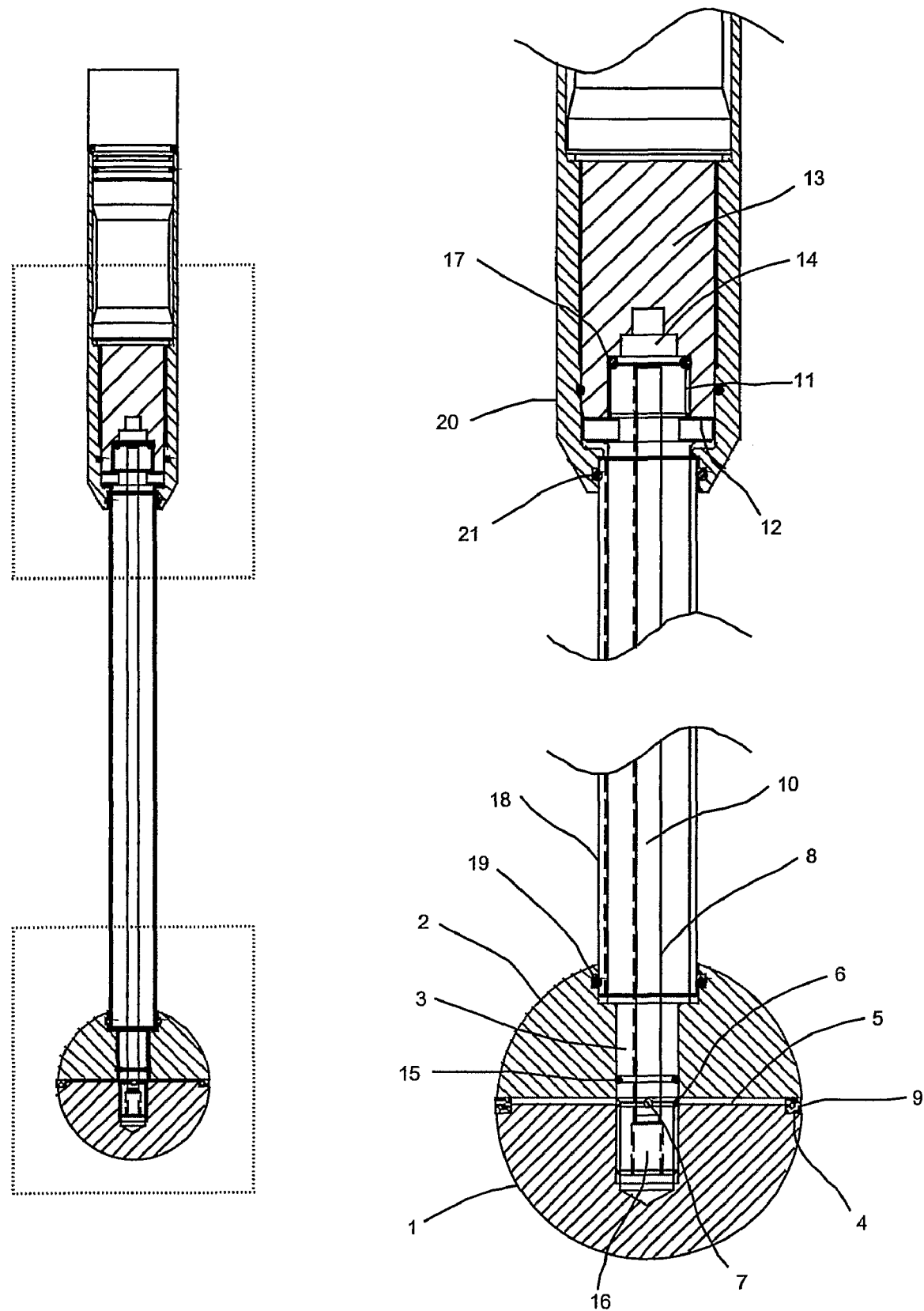
FIG. 1 shows an axial sectional view of a ball penetrometer according to a particular embodiment of the invention, with separate views of end details of the probe enlarged for clarity.

The following modes are described in order to provide a more precise understanding of the subject matter of the present invention.

Preferred Embodiment

With reference to FIG. 1, a ball penetrometer according to the present invention includes a lower hemispherical body 1 and an upper hemispherical body 2, the hemispheres being of equal radius, concentrically arranged and rigidly attached on their axis of symmetry to the lower end of a shaft 3 to form a spherical probe assembly. The hemispherical bodies have uniform outer surfaces of defined or known roughness.

The upper face of lower hemisphere 1 is provided with an outer circumferential groove 4 and a number of radial grooves forming interconnecting passages 5 between the outer groove 4 and a corresponding annular passage 6 formed by a circumferential groove in shaft 3. Annular passage 6 further connects via a number of radial passages 7 to an axial passage 8 in shaft 3. Preferably, though not necessarily, there are four radial grooves forming interconnecting passages 5, and there are two radial passages 7.

Circumferential groove 4 holds a ring 9 of porous material which seats against the faces of lower hemisphere 1 and upper hemisphere 2. Internal passages 5, 6, 7 and 8, are thus fully enclosed and sealed from external water pressure, allowing their volume to be filled with fluid. To minimise the total internal volume a solid rod 10 having a diameter slightly smaller than the diameter of axial passage 8, is inserted along the length of passage 8. The material properties of ring 9 allow the fluid pressure in inner passages 5, 6, 7 and 8 to equilibrate with the external fluid pressure in contact with ring 9.

The upper end of shaft 3 has a threaded connection 11 such that the shoulder 12 forms a rigid attachment of stem 3 to a conventional type of instrumentation module 13 containing an axial load transducer. Axial passage 8 extends through the whole length of stem 3, connecting into a cavity 14 in instrumentation module 13. The internal gallery formed by passage 8 and its adjoining parts is sealed at each end—at the lower end by an o-ring 15 and a thread-sealed screw 16, and at the upper end by an o-ring 17—thus providing a leak-tight path from the porous ring 9 through to the cavity 14, where a pressure transducer is provided to measure the fluid pressure.

The top of upper hemisphere 2 is recessed to freely engage the lower end of an anti-friction sleeve 18. The joint between upper hemisphere 2 and sleeve 18 is sealed by an o-ring 19. Similarly the upper end of sleeve 18 engages the outer sleeve 20 of instrumentation module 13 and is sealed by an o-ring 21. O-rings 19 and 21 thus allow sleeve 18 to 'float' while fully enclosing and sealing shaft 3 without being in contact with it.

In operation, when the penetrometer is thrust into the soil bed, the force resisting penetration is transmitted from the spherical assembly through shaft 3 to the load transducer in module 13. There is only a minute amount of axial movement of the ball and shaft assembly relative to sleeve 18. Any such movement is accommodated by minute flexing of o-ring seals 19 and 21, with negligible effect on the measurement accuracy of the true force acting against the ball. Sleeve 18 fully isolates shaft 3 from soil friction which would otherwise introduce inaccuracies into the desired soil penetration data attributable to the spherical geometry alone.

In a specific, but non-limiting, embodiment the hemispherical bodies 1 and 2, shaft 3, solid rod 10, anti-friction sleeve 18, and associated parts or fittings may be made from a metal, such as heat treatable steel alloys such as 4140 or SAF2205 stainless, or any other suitable materials. Ring 9 of porous material may be made from plastic material such as Porex Technologies 40-100 μm medium P.E. Part No. XS-4904. Internal fluid may be glycerine or a high viscosity mineral oil.

To provide an indication of the dimensions of the preferred penetrometer, in a specific, but non-limiting, embodiment the diameter of hemispherical bodies 1 and 2 is approximately 60 mm, the diameter of shaft 3 is approximately 16 mm, the diameter of solid rod 10 is approximately 4.75 mm, the diameter of axial passage 8 is approximately 5 mm, the diameter of antifriction sleeve 18 is approximately 19 mm, the width of radial interconnecting passages 5 is approximately 1 mm, and the width of radial passages 7 is approximately 1.75 mm. Significant changes could be made to the magnitude of these dimensions in various embodiments encompassed by the present invention.

Instrumentation module 13 may be a Geotech AB transmitter Part No. 41205 or an A.P. van den Berg BV cone adaptor for electric cone type ELC10-CFP that transmits data to a remote processing system which performs known processing techniques and calculations on the data so as to obtain measurements of the forces acting on the ball penetrometer and/or of pore water pressure.

Various Embodiments

Other embodiments of the present invention are possible. According to another embodiment of the present invention the penetrometer may make use of an ellipsoid or spheroid geometry in place of the solid sphere or ball provided by hemispherical bodies 1 and 2. In this embodiment, similar grooves and parts can be utilised, however, remote processing system calculations of forces resisting penetration or withdrawal of the penetrometer would need to be adapted to allow for the change in geometry.

Different numbers, locations and configurations of radial grooves forming interconnecting internal fluid communication passages are possible. For example, grooves may be provided through the body of hemispherical bodies 1 or 2 rather than being formed at the interface of hemispherical bodies 1 and 2. Also, although it is preferred that the porous material be provided as a circumferential ring, the porous material may be provided in other configurations, for example, as part of a ring, covering only an area near the ends of radial passages or as spaced-apart segments. An alternative to the porous ring may be provided by knurling the internal faces of the hemispheres which when held together form a labyrinth of passages interconnecting to annular passage 6.

Further, various geometries of shaft 3, rod 10 and sleeve 18 are possible, it is not essential that these components of the penetrometer be cylindrical, they may have, for example, a rectangular cross-section or a cross-section that varies along their length.

Thus, there has been provided in accordance with the present invention, an improved ball-type penetrometer and associated method of use thereof.

The invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although the preferred embodiment has been described in detail, it should be understood that various changes, substitutions, and alterations can be made by one of ordinary skill in the art without departing from the scope of the present invention.

The invention claimed is:

1. A ball penetrometer for in situ measurement of soft soil properties, including:
   a) a spherical body attached to the end of a shaft, the shaft being of substantially smaller diameter than the diameter of the spherical body and being adapted to associate with a module containing an axial force measuring sensor and data transmitter; and,
   b) a sleeve member enclosing the shaft, the sleeve member being of substantially smaller diameter than the diameter of the spherical body and adapted to isolate the shaft from external soil friction while allowing axial movement of the spherical body and the shaft.

2. The penetrometer as claimed in claim 1, wherein at least part of the surface of the spherical body is provided with or formed of a porous material, the spherical body also including at least one passage providing for fluid communication between the porous material and a pressure sensor.

3. The penetrometer as claimed in claim 2, wherein the porous material is provided as a circumferential porous ring.

4. The penetrometer as claimed in claim 3, wherein the pressure sensor measures pore water pressure of the soil in contact with the porous ring.

5. The penetrometer as claimed in claim 1, wherein the axial force measuring sensor is bi-directional.

6. The penetrometer as claimed in claim 1, wherein at least one flexible sealing member associates the sleeve member with the spherical body, and at least one flexible sealing member associates the sleeve member with housing of the module.

7. The penetrometer as claimed in claim 2, wherein the pressure sensor is located within the module and the shaft includes at least one passage providing fluid communication to the pressure sensor.

8. The penetrometer as claimed in claim 2, wherein there is provided more than one passage arranged radially.

9. The penetrometer as claimed in claim 1, wherein the module is an electronics module.

10. The penetrometer as claimed in claim 9, wherein the penetrometer is interchangeable between different types of electronics modules.

11. The penetrometer as claimed in claim 6, wherein the at least one flexible sealing member is at least one o-ring.

12. The penetrometer as claimed in claim 2, wherein the spherical body is constructed from two hemispherical bodies that together define the at least one passage.

13. A ball penetrometer for in situ measurement of soft soil properties, including:
   a) a spherical body attached to the end of a shaft, the shaft being of substantially smaller diameter than the diameter of the spherical body and being adapted to associate with a module containing an axial force measuring sensor and data transmitter; and,
   b) at least part of the surface of the spherical body provided with or formed of a porous material, the spherical body also including at least one passage providing for fluid communication between the porous material and a pressure sensor, the at least one passage containing an internal fluid held within the spherical body at least partially by the porous material.

14. The penetrometer as claimed in claim 13, including a sleeve member enclosing the shaft, the sleeve member being of substantially smaller diameter than the diameter of the spherical body and adapted to isolate the shaft from external soil friction while allowing axial movement of the spherical body and the shaft.

15. The penetrometer as claimed in claim 13, wherein the porous material is provided as a circumferential porous ring.

16. The penetrometer as claimed in claim 13, wherein the pressure sensor measures pore water pressure of the soil in contact with the porous ring.

17. The penetrometer as claimed in claim 13, wherein the axial force measuring sensor is bi-directional.

18. The penetrometer as claimed in claim 14, wherein at least one flexible sealing member associates the sleeve member with the spherical body, and at least one flexible sealing member associates the sleeve member with housing of the module.

19. The penetrometer as claimed in claim 13, wherein the pressure sensor is located within the module and the shaft includes at least one passage providing fluid communication to the pressure sensor.

20. The penetrometer as claimed in claim 13, wherein there is provided more than one passage arranged radially.

21. The penetrometer as claimed in claim 13, wherein the module is an electronics module.

22. The penetrometer as claimed in claim 21, wherein the penetrometer is interchangeable between different types of electronics modules.

23. The penetrometer as claimed in claim 18, wherein the at least one flexible sealing member is at least one o-ring.

24. The penetrometer as claimed in claim 13, wherein the spherical body is constructed from two hemispherical bodies that together define the at least one passage.

25. A penetrometer for in situ measurement of soft soil properties, including:
   a) an ellipsoidal body attached to the end of a shaft, the shaft being of substantially small diameter than the diameter of the ellipsoidal body and being adapted to associate with a module containing an axial force measuring sensor and data transmitter; and,
   b) a sleeve member enclosing the shaft, the sleeve member being of substantially smaller diameter than the diameter of the ellipsoidal body and adapted to isolate the shaft from external soil friction while allowing axial movement of the ellipsoidal body and the shaft.

26. A penetrometer for in situ measurement of soft soil properties, including:
   a) an ellipsoidal body attached to the end of a shaft, the shaft being of substantially smaller diameter than the diameter of the ellipsoidal body and being adapted to associate with a module containing an axial force measuring sensor and data transmitter; and, b) at least part of the surface of the ellipsoidal body provided with or formed of a porous material, the ellipsoidal body also including at least one passage providing for fluid communication between the porous material and a pressure sensor, the at least one passage containing an internal fluid held within the ellipsoidal body at least partially by the porous material.

27. A method of in situ measurement of soft soil properties using a ball penetrometer, the ball penetrometer including a spherical body attached to an end of a shaft, the shaft being of substantially smaller diameter than the diameter of the spherical body and being adapted to associate with a module containing an axial force measuring sensor and data transmitter, and a sleeve member enclosing the shaft, the sleeve member being of substantially smaller diameter than the diameter of the spherical body and adapted to isolate the shaft from external soil friction while allowing axial movement of the spherical body and the shaft, the method including the steps of:
 a) forcing the ball penetrometer to penetrate a soil bed at a known rate;
 b) measuring the force resisting penetration of the spherical body into the soil bed; and,
 c) transmitting measurement data to a remote operating station for processing.

28. A method of in situ measurement of soft soil properties using a ball penetrometer, the ball penetrometer including a spherical body attached to an end of a shaft, the shaft being of substantially smaller diameter than the diameter of the spherical body and being adapted to associate with a module containing an axial force measuring sensor and data transmitter, and at least part of the surface of the spherical body provided with or formed of a porous material, the spherical body also including at least one passage providing for fluid communication between the porous material and a pressure sensor, the at least one passage containing an internal fluid held within the spherical body at least partially by the porous material, the method including the steps of:
 a) forcing the ball penetrometer to penetrate a soil bed at a known rate;
 b) measuring the force resisting penetration of the spherical body into the soil bed;
 c) measuring the pore water pressure of the soil in contact with the porous material by measuring the pressure of the internal fluid; and,
 d) transmitting measurement data to a remote operating station for processing.

29. The method as claimed in claim 27, wherein additional steps are provided between steps (b) and (c) as:
 b1) withdrawing the ball penetrometer from the soil bed at a known rate; and
 b2) measuring the force resisting removal of the spherical body from the soil bed.

30. The method as claimed in claim 27, wherein at least part of the surface of the spherical body is provided with or formed of a porous material, the spherical body also including at least one passage providing for fluid communication between the porous material and a pressure sensor, and the method includes measuring the pore water pressure in contact with the porous material.

31. The method as claimed in claim 27, wherein measurements are taken as a function of depth into the soil bed or of time.

32. The method as claimed in claim 27, wherein the ball penetrometer is deployed from an apparatus on the seafloor.

33. The method as claimed in claim 32, wherein a connector rod or series of connector rods are provided to facilitate deployment of the ball penetrometer and progressively extend penetration into the seabed.

34. The method as claimed in claim 27, wherein the measurement data is transmitted wirelessly from the module to a remotely operated seabed system.

35. The method as claimed in claim 27, wherein the ball penetrometer is deployed via a wireline drillstring and measurement data is transmitted to the remote operating station via a wired electrical connection.

36. The penetrometer as claimed in claim 3, wherein the pressure sensor is located within the module and the shaft includes at least one passage providing fluid communication to the pressure sensor.

37. The penetrometer as claimed in claim 3, wherein there is provided more than one passage arranged radially.

38. The method as claimed in claim 28, wherein additional steps are provided between steps (b) and (c) as:
 b1) withdrawing the ball penetrometer from the soil bed at a known rate; and
 b2) measuring the force resisting removal of the spherical body from the soil bed.

* * * * *